(12) United States Patent
Deckard et al.

(10) Patent No.: US 9,108,026 B2
(45) Date of Patent: Aug. 18, 2015

(54) SPRING ACTION MEDICAL DEVICE

(75) Inventors: Michael D. Deckard, Solsberry, IN (US); Michael W. Hardert, Bloomington, IN (US); Thomas A. Kay, Jr., Bloomington, IN (US); William F. Moore, Bloomington, IN (US); James C. Elsesser, Bloomington, IN (US); David C. Lentz, Bloomington, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 390 days.

(21) Appl. No.: 13/379,975

(22) PCT Filed: Jul. 8, 2010

(86) PCT No.: PCT/US2010/041382
§ 371 (c)(1),
(2), (4) Date: Mar. 8, 2012

(87) PCT Pub. No.: WO2011/005971
PCT Pub. Date: Jan. 13, 2011

(65) Prior Publication Data
US 2012/0165850 A1    Jun. 28, 2012

Related U.S. Application Data

(60) Provisional application No. 61/224,232, filed on Jul. 9, 2009.

(51) Int. Cl.
*A61B 17/34* (2006.01)
*A61M 25/09* (2006.01)
*A61B 17/22* (2006.01)

(52) U.S. Cl.
CPC .... *A61M 25/09025* (2013.01); *A61B 17/22012* (2013.01); *A61B 2017/22038* (2013.01); *A61B 2017/22069* (2013.01); *A61B 2017/22094* (2013.01)

(58) Field of Classification Search
CPC ............. A61B 17/34; A61B 17/22012; A61B 2017/22094; A61B 2017/22038; A61B 2017/22069; A61B 17/320758; A61M 25/09025; A61M 25/09041; A61M 2025/09175; A61M 25/0102; A61M 25/0105; A61F 2002/4681
USPC .......... 606/108, 185, 127–128, 159; 600/585; 604/270, 528, 510, 585, 35, 118, 131, 604/173, 532; 500/585
See application file for complete search history.

(56) References Cited

U.S. PATENT DOCUMENTS 2,617,651 A    11/1952  Gerhold
2,639,709 A    5/1953   Volgenau
(Continued)

FOREIGN PATENT DOCUMENTS

DE    40 36 570 A1    5/1992
DE    41 30 042 A1    3/1993
FR    2 645 009 A1    10/1990

*Primary Examiner* — Amy R Weisberg
(74) *Attorney, Agent, or Firm* — Brinks Gilson & Lione

(57) ABSTRACT

A spring action medical device includes a spring that may propel a hammer component in a distal direction when the spring is released from a loaded state. When propelled forward by the spring, the hammer component makes contact with a distal tip of the medical device. The distal tip may then transfer a force to an external object, such as an occlusion in a body lumen.

15 Claims, 5 Drawing Sheets

(56) References Cited

U.S. PATENT DOCUMENTS

| | | | |
|---|---|---|---|
| 3,552,384 A | 1/1971 | Pierie et al. | |
| 4,215,703 A | 8/1980 | Willson | |
| 4,307,722 A | 12/1981 | Evans | |
| 4,456,017 A | 6/1984 | Miles | |
| 4,549,535 A * | 10/1985 | Wing | 601/108 |
| 4,561,439 A | 12/1985 | Bishop et al. | |
| 4,676,249 A | 6/1987 | Arenas et al. | |
| 4,757,827 A | 7/1988 | Buchbinder et al. | |
| 5,172,701 A * | 12/1992 | Leigh | 600/566 |
| 5,250,034 A | 10/1993 | Appling et al. | |
| 5,363,736 A * | 11/1994 | Huang | 89/1.14 |
| 5,476,502 A | 12/1995 | Rubin | |
| 5,505,261 A * | 4/1996 | Huber et al. | 166/297 |
| 5,573,010 A | 11/1996 | Pflugbeil | |
| 5,743,900 A | 4/1998 | Hara | |
| 5,776,079 A | 7/1998 | Cope et al. | |
| 5,891,086 A * | 4/1999 | Weston | 604/70 |
| 5,906,623 A | 5/1999 | Peterson | |
| 5,957,886 A * | 9/1999 | Weston | 604/68 |
| 5,972,019 A | 10/1999 | Engelson et al. | |
| 6,146,339 A | 11/2000 | Biagtan et al. | |
| 6,183,420 B1 | 2/2001 | Douk et al. | |
| 6,348,041 B1 | 2/2002 | Klint | |
| 6,371,939 B2 * | 4/2002 | Bergens et al. | 604/156 |
| 6,685,696 B2 | 2/2004 | Fleischhacker et al. | |
| 7,470,237 B2 * | 12/2008 | Beckman et al. | 600/564 |
| 8,114,119 B2 * | 2/2012 | Spivey et al. | 606/205 |
| 2001/0039394 A1 * | 11/2001 | Weston | 604/72 |
| 2003/0163064 A1 | 8/2003 | Vrba et al. | |
| 2003/0208885 A1 * | 11/2003 | Zaltron | 16/430 |
| 2004/0035491 A1 * | 2/2004 | Castellano | 141/27 |
| 2004/0254526 A1 * | 12/2004 | Weston | 604/68 |
| 2004/0254599 A1 * | 12/2004 | Lipoma et al. | 606/181 |
| 2004/0260201 A1 | 12/2004 | Mueller, Jr. | |
| 2004/0267307 A1 | 12/2004 | Bagaoisan et al. | |
| 2005/0096586 A1 * | 5/2005 | Trautman et al. | 604/46 |
| 2005/0113862 A1 | 5/2005 | Besselink et al. | |
| 2005/0192530 A1 * | 9/2005 | Castellano | 604/70 |
| 2005/0277980 A1 | 12/2005 | Yassinzadeh | |
| 2006/0293612 A1 | 12/2006 | Jenson et al. | |
| 2007/0066935 A1 * | 3/2007 | Morishita et al. | 604/68 |
| 2007/0088377 A1 * | 4/2007 | LeVaughn et al. | 606/181 |
| 2007/0203427 A1 * | 8/2007 | Vetter et al. | 600/564 |
| 2007/0208273 A1 * | 9/2007 | Vetter et al. | 600/567 |
| 2007/0219565 A1 * | 9/2007 | Saadat | 606/142 |
| 2008/0077165 A1 | 3/2008 | Murphy | |
| 2009/0082851 A1 | 3/2009 | Brumleve et al. | |
| 2011/0245736 A1 * | 10/2011 | Foehrenbach | 601/4 |
| 2012/0065615 A1 * | 3/2012 | Boyd et al. | 604/500 |
| 2013/0226098 A1 * | 8/2013 | Tokumoto et al. | 604/228 |

\* cited by examiner

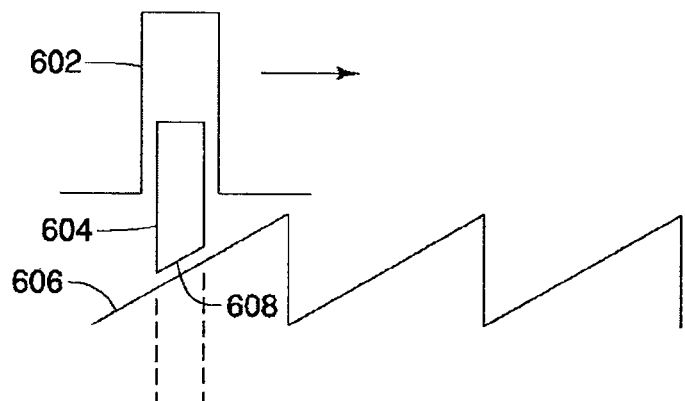
Figure 6b
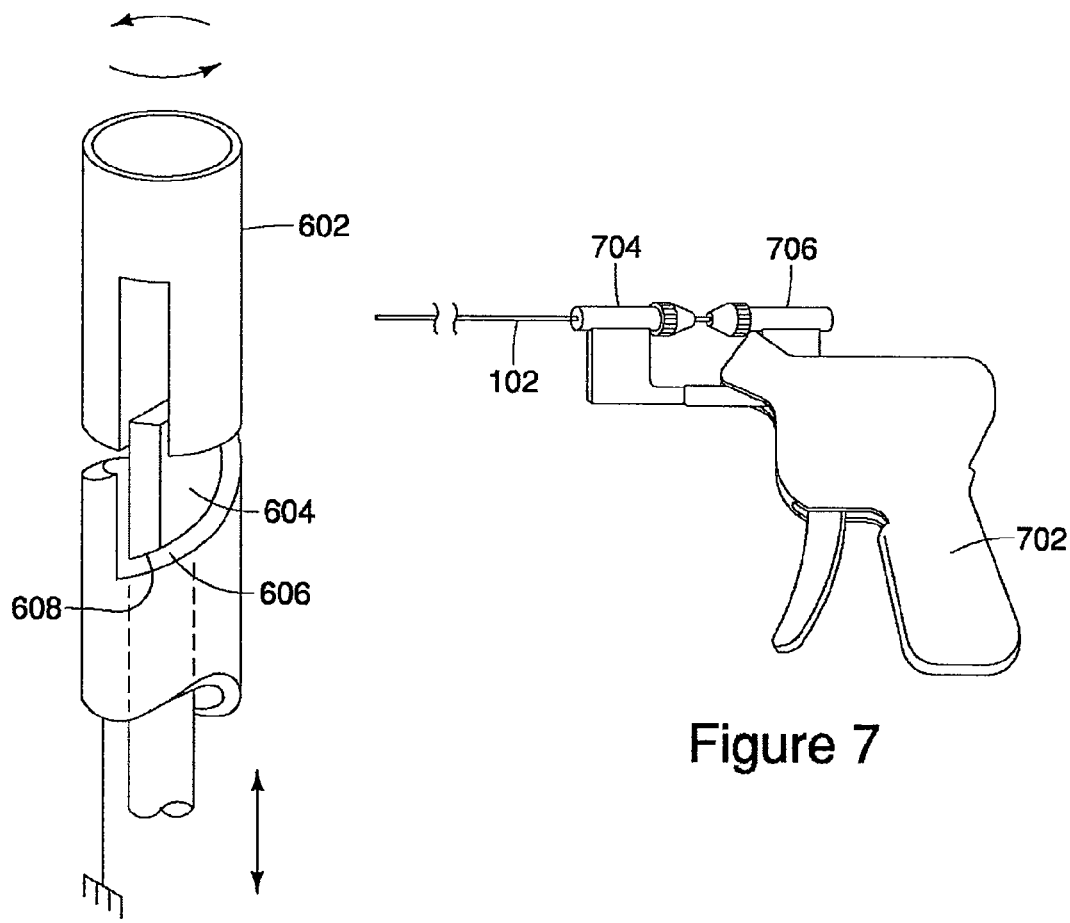
Figure 6a
Figure 7

SPRING ACTION MEDICAL DEVICE

PRIORITY CLAIM

This application is a 35 U.S.C. §371 filing based on International Application Serial No. PCT/US2010/041382, filed Jul. 8, 2010, which claims the benefit of U.S. Provisional Application No. 61/224,232, filed Jul. 9, 2009, both of which are hereby incorporated by reference.

TECHNICAL FIELD

This application relates to medical devices, and in particular to spring action medical devices and methods of using spring action medical devices.

BACKGROUND

Some medical devices, such as wire guides and catheters, may be inserted into a patient's vascular system or other body lumen. Wire guides and catheters may be used in angioplasty procedures, diagnostic and interventional procedures, percutaneous access procedures, or radiological and neuroradiological procedures in general. Wire guides are commonly used in vascular procedures to introduce a wide variety of medical devices (e.g., catheters) into the vascular system. Catheters may also be used to provide access into the vascular system.

Medical devices may encounter various challenges as they are guided through a patient's vascular system or other body lumen. For example, a procedure may require a physician to steer a wire guide or catheter through tortuous passageways before reaching a destination. In such a procedure, the device needs sufficient stiffness to be pushed along the path while remaining flexible enough to pass through the tortuous passageways without causing damage. Additionally, the patient's vascular system or other body lumen may contain occlusions that impede the device along its path. It may be difficult for some medical devices to pass through occlusions. These occlusions may also impede fluid flow in the body lumen. Therefore, a need exists for an improved medical device for passing through and/or clearing occlusions.

BRIEF SUMMARY

In one implementation, a medical device includes a distal tip, a spring, and a hammer component disposed between the distal tip and the spring. The spring is configured to provide a force when released from a loaded state to propel the hammer component in a distal direction toward the distal tip to strike the distal tip.

In another implementation, a medical device includes a body portion, a distal tip disposed at a distal end of the body portion, a support structure on an inner surface of the body portion, a hammer component, a spring, and a trigger wire. The spring is disposed between the hammer component and the support structure. The trigger wire is coupled with the hammer component in a configuration where movement of the trigger wire in a proximal direction relative to the body portion retracts the hammer component and compresses the spring into a loaded state between the hammer component and the support structure. The spring is configured to provide a force when released from the loaded state to propel the hammer component forward in a distal direction relative to the body portion to strike the distal tip.

In another implementation, a method of using a medical device is provided. A spring of the medical device is placed in a loaded state by retracting a trigger wire of the medical device. A distal tip of the medical device is positioned to abut an occlusion in a body lumen or to be within a distal tip movement range of the occlusion in the body lumen. The spring is released from the loaded state to propel a hammer component of the medical device in a distal direction to strike the distal tip and transfer a force from the distal tip to the occlusion.

BRIEF DESCRIPTION OF THE DRAWINGS

The components in the figures are not necessarily to scale. Moreover, in the figures, like referenced numerals designate corresponding parts throughout the different views.

FIGS. 6a and 6b illustrate one embodiment of an actuator for a spring action medical device.

FIG. 7 illustrates another embodiment of an actuator for a spring action medical device.

DETAILED DESCRIPTION

Figure 1:
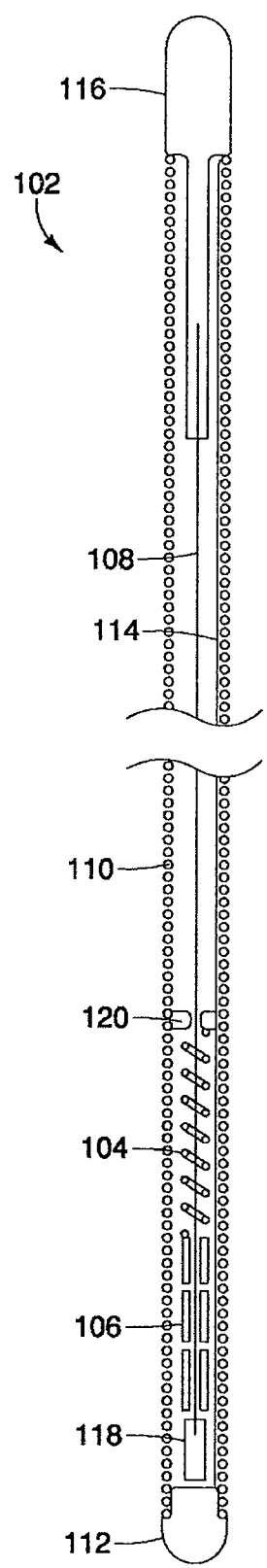
FIG. 1 shows one embodiment of a spring action wire guide.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As used herein, the term "proximal" refers to a portion of the medical device closest to a user when placing the medical device in a patient, and the term "distal" refers to a portion of the medical device closest to the end inserted into the patient's body.

FIG. 1 shows one embodiment of a spring action wire guide 102. The wire guide 102 includes a spring 104, a hammer component 106, a trigger wire 108, an outer wire guide body 110, a distal tip 112, a safety wire 114, and a handle 116. As described in greater detail below, the spring 104 is configured to propel the hammer component 106 forward in a distal direction when the spring 104 is released from a loaded state. When biased forward by the spring 104, the distal-most segment 118 (e.g., hammer head) of the hammer component 106 makes contact with the distal tip 112. The distal tip 112 may then transfer a force to an external object. In some implementations, the distal tip 112 may transfer the force to an occlusion in a vascular passage or other body lumen in attempt to break apart, clear, or pass through the occlusion.

The spring 104 is an elastic device that stores mechanical energy. The spring 104 may be a wire spring, a coil spring, a flat spring, or another resilient/compressive structure that may be a separate component or built into another component of the wire guide 102. In the implementation of FIG. 1, the spring 104 may be a coil spring disposed about a portion of the trigger wire 108. For example, the spring 104 may be disposed about the trigger wire 108 between a support structure 120 and the hammer component 106. The spring 104 may be formed from any material suitable for forming expandable springs, such as medical grade stainless steel, a stainless steel alloy, Elgiloy, Nivaflex, a super-elastic material including a nickel-titanium alloy (e.g., Nitinol), a linear-elastic material, or combinations of these materials. In other implementations, other suitable spring materials may be used. The spring may be a micro or miniature type spring made by the Motion Dynamics Corporation.

In the implementation of FIG. 1, the spring 104 is in a loaded or charged state when compressed under load. When the spring 104 is released from the compressed state, the spring 104 provides an activation force against the hammer component 106 to push the hammer component 106 forward in the distal direction. In other implementations, the wire guide 102 may be modified to include a tension spring that is extended under load and then released to provide an actuation force against the hammer component 106.

In one implementation, the spring 104 may travel up to an inch or two very quickly. In other implementations, the spring 104 may travel more than two inches very quickly. The spring 104 may be formed to have a spring constant that provides a desired force according to Hooke's law, $F=-kx$, where $F$ represents the force exerted by the spring 104 when released, $k$ represents the spring constant, and $x$ represents the distance that the spring 104 is compressed from a relaxed state. To increase the force provided by the spring 104, the spring 104 may be compressed to a greater degree before release or may be formed to have a larger spring constant. In some implementations, a large spring force is desired to help break apart, clear, or pass through occlusions in the vascular system. In other implementations, a smaller spring force may be desired to avoid damage to the vascular system. The amount of spring compression and the spring constant may therefore be selected or varied to meet the needs of the intended application for the wire guide 102.

The hammer component 106 provides a mass that may be propelled by the spring 104 to cause the distal-most segment 118 of the hammer component 106 to strike the distal tip 112. The hammer component may be formed of a dense metal (e.g., palladium, platinum, or the like) or another material. A radiopaque material may be used to increase the visibility of the hammer component 106 when the wire guide 102 is within the body of a patient.

The hammer component 106 may be disposed about a portion of the trigger wire 108. For example, the spring 104 may be disposed about the trigger wire 108 between the spring 104 and the distal end of the trigger wire 108. In one implementation, the hammer component 106 may be constrained to move only along the longitudinal axis of the wire guide 102.

The hammer component 106 may be formed from one or more separate components. The hammer component 106 shown in FIG. 1 comprises multiple hollow cylindrical segments that are slidably threaded onto the trigger wire 108. The trigger wire 108 may pass through the hollow center of the individual cylindrical segments. In the implementation of FIG. 1, the individual segments may move freely along a portion of the trigger wire 108. The multiple segments may allow the hammer component 106 to turn more easily through tortuosities in the vasculature. In other implementations, the hammer component 106 may be formed as a unitary component.

The trigger wire 108 may be coupled with a distal-most segment 118 of the hammer component 106, which in the implementation of FIG. 1 is a solid cylindrical segment. In other implementations, the trigger wire 108 may be coupled with another part of the hammer component 106. The trigger wire 108 may be connected with the hammer component 106 by soldering, welding, crimping, or the like. The other segments of the hammer component 106 may be slidably threaded onto the trigger wire 108. When the trigger wire 108 is pulled back in a proximal direction, the distal-most segment 118 is retracted with the trigger wire 108. The space between the individual segments may be reduced as the distal-most segment 118 is drawn in the proximal direction. The individual segments may abut while the spring 104 is being compressed.

The trigger wire 108 may comprise a core element, solid shaft, suture, cable, wire, or mandrel of the wire guide 102. The trigger wire 108 has a distal end and a proximal end. The distal end of the trigger wire 108 may be coupled with the hammer component 106. For example, the distal end of the trigger wire 108 may be coupled with distal-most segment 118 of the hammer component 106. The proximal end of the trigger wire 108 may be coupled with the handle 116 or may be free to exit the proximal end of the outer wire guide body 110. The handle 116 may be used to pull the trigger wire 108 in a proximal direction. Alternatively or additionally, the handle may be used to push the trigger wire 108 in a distal direction or twist the trigger wire 108. Where the handle 116 is used to twist the trigger wire 108, the wire guide 102 may include a torque transmitting feature (e.g., a polygonal cross-section or a key and keyway) between the trigger wire 108 and the outer wire guide body 110. In addition to controlling the spring 104, such manipulations may also steer the wire guide 102 along its path through the vascular system or other lumen. The handle 116 may be formed to have a low profile so that a medical device (e.g., a catheter) may pass over the handle and continue to pass over the remainder of the wire guide 102 unimpeded.

The trigger wire 108 may be formed of a suitable metallic material such as medical grade stainless steel, a stainless steel alloy, Elgiloy, Nivaflex, a super-elastic material including a nickel-titanium alloy (e.g., Nitinol), a linear-elastic material, or combinations of these materials. In other implementations, other suitable trigger wire materials may be used. The trigger wire 108 may include a radiopaque material, such as platinum or gold. Inclusion of a radiopaque material may increase the visibility of the wire guide 102 within the body of a patient. In some implementations, a radiopaque material may be included in other portions of the wire guide 102, such as in the outer wire guide body 110, the spring 104, the hammer component 106, and/or the distal tip 112.

It will be appreciated that the trigger wire 108 may take one of many different shapes. In some implementations, the trigger wire 108 has a circular cross-sectional shape. In other implementations, the trigger wire 108 has a rectangular cross-sectional shape. In yet other implementations, the cross-section of the trigger wire 108 assumes different shapes along the length of the trigger wire 108.

The flexibility of the wire guide 102 may be constant or may vary along the length of the wire guide 102. The trigger wire 108 and/or the outer wire guide body 110 may have a cross-sectional area that remains substantially constant along its length. Alternatively, the trigger wire 108 and/or the outer wire guide body 110 may have a cross-sectional area that varies along their respective lengths. In one implementation, the trigger wire 108 and/or the outer wire guide body 110 has a cross-sectional area that diminishes gradually or stepwise at an increasing distance from the proximal end of the wire guide 102 such that the trigger wire 108 and/or the outer wire guide body 110 tapers to a smaller diameter toward their respective distal ends. For example, the trigger wire 108 and/or the outer wire guide body 110 may include a tapered distal end portion. The tapered distal end portion may increase the flexibility of the distal end of the wire guide 102. The flexibility of the wire guide 102 may also be controlled by characteristics of other components of the wire guide 102, such as the spring 104 or the hammer component 106.

The outer wire guide body 110 may be disposed about at least a portion of the trigger wire 108. The outer wire guide body 110 may be a cannula, sheath, tube, helical coil, or a combination thereof. The outer wire guide body 110 may be compressible or uncompressible. In one implementation, as shown in FIG. 1, the outer wire guide body 110 may comprise a coil wrapped about the trigger wire 108. In another implementation, the outer wire guide body 110 may comprise a solid tube. The outer wire guide body 110 may be formed of a suitable metallic material such as medical grade stainless steel, a stainless steel alloy, Elgiloy, Nivaflex, a super-elastic material including a nickel-titanium alloy (e.g., Nitinol), a linear-elastic material, or combinations of these materials. In other implementations, other materials may be used.

The outer wire guide body 110 is sized to slidably receive a portion of the trigger wire 108 such that that trigger wire 108 is longitudinally movable relative to the outer wire guide body 110. In this way, a physician may use the handle 116 to push, pull, or twist the trigger wire 108 relative to the outer wire guide body 110. For example, when the physician pulls the handle 116 proximally relative to the outer wire guide body 110, the hammer component 106 is retracted, which places the spring 104 in a compressed state between the hammer component 106 and the support structure 120 of the outer wire guide body 110. The support structure 120 may support the proximal end of the spring 104. The support structure 120 may be formed on the outer wire guide body 110. For example, the support structure 120 may be a lip or rim formed in the outer wire guide body 110.

In one implementation, the trigger wire 108 may be coated with a material to allow it to slide through the outer wire guide body 110 more easily. In another implementation, the inner surface of the outer wire guide body 110 may be coated. The coating may be a material that reduces the coefficient of friction between the trigger wire 108 and the outer wire guide body 110. For example, the coating may include a polymer, such as a fluoropolymer. In one implementation, the coating may be polytetrafluoroethylene ("PTFE").

The distal tip 112 of the wire guide 102 may be disposed at a distal end of the outer wire guide body 110. In one implementation, the distal tip 112 is an integral portion of the outer wire guide body 110. In another implementation, the distal tip 112 is a member connected with the outer wire guide body 110. For example, the distal tip 112 may be attached to the outer wire guide body 110 by adhesive, solder, laser welding, crimping, or other attachment method. In the implementation of FIG. 1, the distal tip 112 has an atraumatic shape, such as a rounded front or a front of flexible material. For example, the distal tip 112 may be a solder ball or a sphere. In another implementation, the distal tip 112 may have a shape that is designed to pierce through occlusions. For example, the distal tip 112 may be a trocar, sharpened end, or other pointed structure. The distal tip 112 may have a conical shape with a truncated or rounded nose to push any stenotic material outward and create a passageway through an occlusion. Additionally, the distal tip 112 may have helical features which impart a rotational motion on the wire guide 102 to drill or auger through the stenosis.

The wire guide 102 may include a safety wire 114 that connects the distal tip 112 (or some other distal end portion of the outer wire guide body 110) to a portion of the outer wire guide body 110. In the implementation of FIG. 1, the safety wire 114 connects with the distal tip 112 and a proximal end of the outer wire guide body 110. The safety wire 114 may run the length of the interior of the wire guide 102 to ensure longitudinal integrity of the outer wire guide body 110. The safety wire 114 may limit longitudinal movement of the distal tip 112 (or some other distal end portion of the outer wire guide body 110) relative to the remainder of the outer wire guide body 110. When the safety wire 114 is connected between the distal tip 112 and a portion of the outer wire guide body 110, the distal tip 112 may only move forward to the degree allowed by the safety wire 114. When the safety wire 114 is connected between a first portion (e.g., a distal portion) of the outer wire guide body 110 and a second portion (e.g., a proximal portion) of the outer wire guide body 110, then the distal tip 112 may have some room to move in response to contact from the hammer component 106 due to flexibility in the portion of the outer wire guide body 110 not constrained by the safety wire 114. The safety wire 114 may constrain substantially all distal movement of the tip or may be designed to allow some distal movement. Even if the safety wire 114 constrains the distal tip 112 from moving forward when struck by the hammer components, the distal tip 112 may still transfer force from the hammer component 106 to an external object, such as an occlusion in a vascular passageway. For example, the distal tip 112 may be positioned to abut the external object prior to being struck by the hammer components. The force from the hammer components may then transfer through the constrained distal tip 112 and to the external object. Where the external object is an occlusion in a vascular passageway, the transferred force may serve to break apart, clear, or pass through the occlusion.

Figure 2:
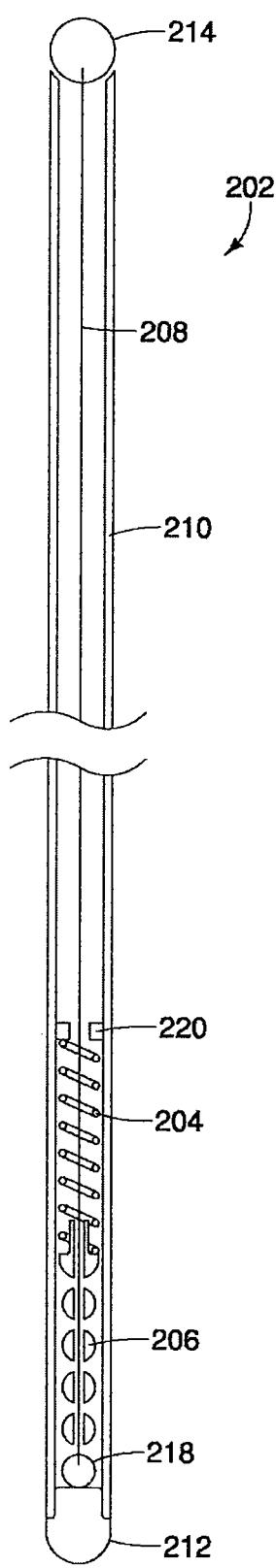
FIG. 2 shows another embodiment of a spring action wire guide.

FIG. 2 shows another embodiment of a spring action wire guide 202. The wire guide 202 includes a spring 204, a hammer component 206, a trigger wire 208, an outer wire guide body 210, a distal tip 212, and a handle 214. Many of the components of the wire guide 202 of FIG. 2 have a similar construction/function as the corresponding components of the wire guide 102 of FIG. 1. For example, the description herein for the spring 104, the trigger wire 108, the distal tip 112, and the support structure 120 may also apply to the spring 204, the trigger wire 208, the distal tip 212, and the support structure 220, respectively. The outer wire guide body 210 in FIG. 2 performs a similar function as the outer wire guide body 110 in FIG. 1. FIG. 1 illustrates one example of a coil wire guide body while FIG. 2 illustrates one example of a laser-cut cannula body (e.g., a laser-cut body). The handle 214 of FIG. 2 performs a similar function as the handle 116 of FIG. 1. The handles 116 and 214 are shown to have different shapes.

The hammer component 206 shown in FIG. 2 comprises a hollow bead-based hammer assembly. Specifically, the hammer component 206 may comprise multiple bead segments that are slidably threaded onto the trigger wire 208. The trigger wire 208 may pass through the hollow center of the individual bead segments. The bead segments may be rounded to allow the segments to more easily pass through the outer wire guide body 210. Alternatively, the hammer component 206 may be formed from beads of a different shape, such as rectangular (e.g., cube-like) or cylindrical (e.g., tube-like). In some implementations, the hammer component 206 may be formed from multiple segments to allow the hammer component 206 to bend more easily and traverse tortuous vasculature. In other implementations, the hammer component 206 may be formed as a unitary component.

The trigger wire 208 may be coupled to a distal-most segment 218 of the hammer component 206. In other implementations, the trigger wire 208 may be coupled with another part of the hammer component 206. The trigger wire 208 may be connected with the distal-most segment 218 of the hammer component 206 by soldering, welding, crimping, or the like. The other segments of the hammer component 206 may then be slidably threaded onto the trigger wire 208. When the trigger wire 208 is pulled back in a proximal direction the distal-most segment 218 may be retracted with the trigger wire 208. The space between the coils of the spring 204 may be reduced as the distal-most segment 218 is drawn in the distal direction so as to bias the sprig 204 against the support structure 220. The individual coils may abut when the spring 204 is being compressed. When the spring 204 is released from the compressed state, the spring 204 biases (e.g., pushes/propels) the hammer component 206 and the distal-most segment 218 against the distal tip 212.

The cannula body 210 may limit some longitudinal movement of the distal tip 212 relative to the remainder of the wire guide 202 when struck by the hammer components. When the distal-most segment 218 of the hammer component 206 strikes the distal tip 212, the distal tip 212 may only move forward to the degree allowed by the cannula body 210. The cannula body 210 may constrain substantially all distal movement of the tip or may be designed to allow some distal movement. Even if the cannula body 210 constrains the distal tip 212 from moving forward when struck by the distal-most segment 218 of the hammer component 206, the distal tip 212 may still transfer force from the hammer components to an external object, such as an occlusion in a vascular passageway. For example, the distal tip 212 may be positioned to abut the external object prior to being struck by the distal-most segment 218 of the hammer component 206. The force from the hammer components may then transfer through the constrained distal tip 212 and into the external object. Where the external object is an occlusion in a vascular passageway, the transferred force may serve to break apart, clear, or pass through the occlusion.

Figure 3:
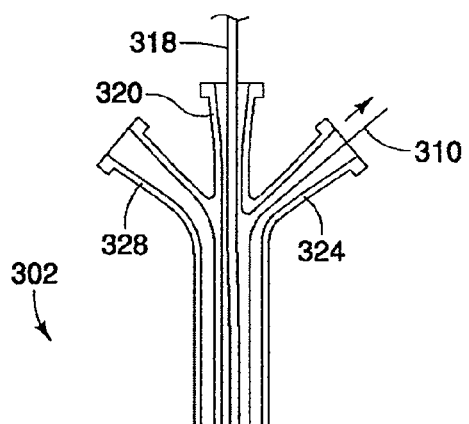
FIG. 3 shows one embodiment of a spring action catheter.
Figure 3:
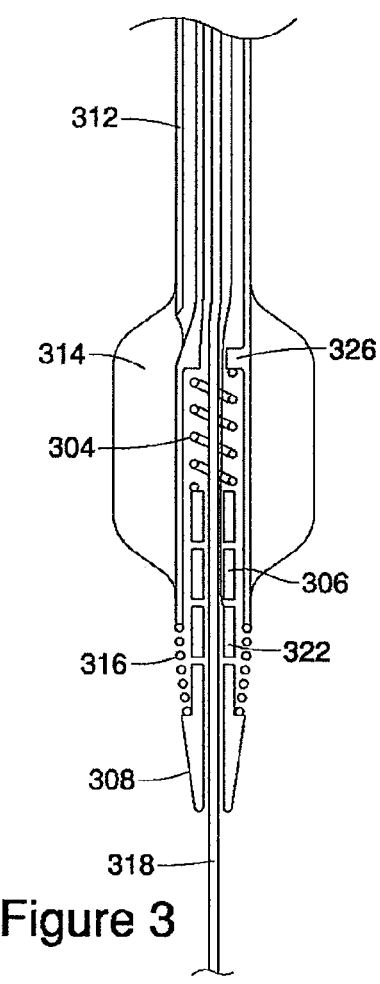

FIG. 3 shows one embodiment of a spring action catheter 302. The catheter 302 includes a spring 304, a hammer component 306, a distal tip 308, a trigger wire 310, an outer catheter body 312, a balloon 314, and a recoil spring 316.

The catheter 302 may include a passageway that allows the catheter 302 to be placed over another medical device, such as a wire guide 318. An opening 320 provides access to the passageway through the catheter 302. As shown in FIG. 3, the wire guide 318 may pass through the catheter 302 and extend out from the distal and proximal ends of the catheter 302. The opening 320 and passageway may also serve as a lumen for the aspiration of dislodged emboli or other material.

The spring 304 illustrated in FIG. 3 is configured to provide a force to push the hammer component 306 forward in a distal direction when the spring 304 is released from a compressed state. The spring 304 may have a similar construction/function as the spring 104 of FIG. 1. For example, the description herein for the spring 104 may also apply to the spring 304.

The hammer component 306 provides a mass that may be propelled by the spring 304 to strike the distal tip 308. The hammer component 306 may have a similar construction/function as the hammer component 106 of FIG. 1. For example, the description herein for the hammer component 106 may also apply to the hammer component 306. The hammer component 306 may be disposed about a portion of the trigger wire 310. In FIG. 3, the hammer component 306 may be formed as a hollow cylindrical segment-based hammer assembly. The trigger wire 310 may be coupled with one or more of the segments, such as the distal-most segment 322 of the hammer component 306. When the trigger wire 310 is pulled back in a proximal direction, the hammer components may be retracted with the trigger wire 108.

The catheter 302 may include an opening 324 that provides access to a passageway for the trigger wire 310. The trigger wire 310 may comprise a core element, suture, cable, wire, or mandrel, with a similar structure and function as the trigger wire 108 described in connection with FIG. 1. The description herein for the trigger wire 108 may also apply to the trigger wire 310. The distal end of the trigger wire 310 may be coupled with the distal-most segment 322 of the hammer component 306. The proximal end of the trigger wire 310 may be coupled with a handle or may be free to exit the proximal end of the catheter 302.

The trigger wire 310 may be movable relative to the outer catheter body 312. When a physician pulls the trigger wire 310 proximally relative to the outer catheter body 312, the distal-most segment 322 of the hammer component 306 is retracted which places the spring 304 in a compressed state between the hammer component 306 and a support structure 326 of the outer catheter body 312. The support structure 326 may support the proximal end of the spring 304. The support structure 326 may be formed on the outer catheter body 312. For example, the support structure 326 may be a lip or rim formed in the outer catheter body 312.

The distal tip 308 is disposed at a distal end of the catheter 302. In one implementation, the distal tip 308 comprises an atraumatic shape, such as a rounded tip or a tip of flexible material. In another implementation, the distal tip 308 may have a shape that is designed to pierce through occlusions. For example, as shown in FIG. 3, the distal tip 308 may have a pointed tip. The distal tip 308 may have a conical shape to push any stenotic material outward and create a passageway through an occlusion.

The catheter 302 may include an opening 328 that provides access to the balloon 314. The balloon 314 may be configured like an angioplasty balloon. The opening 328 may be used to expand the balloon 314 to make contact with the vessel wall. The balloon 314, when expanded, serves to anchor the catheter 302 in place within the vessel.

To activate the spring action component of the catheter 302, the spring 304 is released from a compressed state to provide a force to push the hammer component 306 forward in a distal direction. When the distal-most segment 322 of the hammer component 306 strikes the distal tip 308, the tip 308 may move forward in the distal direction. The catheter 302 may include the recoil spring 316 to allow the distal tip 308 to move forward without dislodging the balloon 314 from its connection with the vessel wall.

Figure 4:
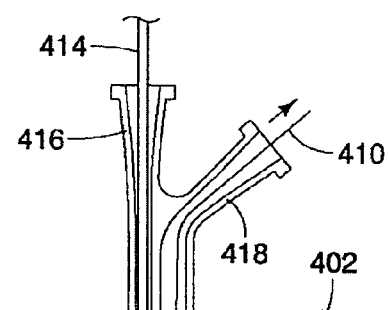
FIG. 4 shows another embodiment of a spring action catheter.
Figure 4:
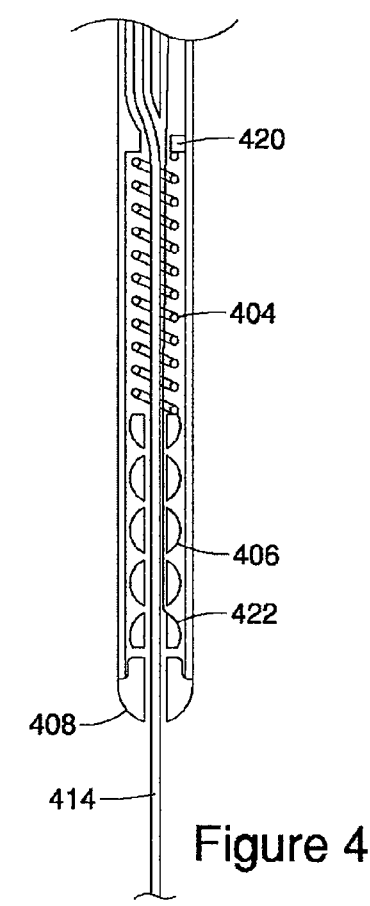

FIG. 4 shows another embodiment of a spring action catheter 402. The catheter 402 includes a spring 404, a hammer component 406, a distal tip 408, a trigger wire 410, and an outer catheter body 412. Many of the components of the catheter 402 of FIG. 4 have a similar construction/function as the corresponding components of the catheter 302 of FIG. 3. For example, the description herein for the spring 304, the trigger wire 310, the outer catheter body 312, the wire guide 318, the opening 320, the opening 324, and the support structure 326 may also apply to the spring 404, the trigger wire 410, the outer catheter body 412, the wire guide 414, the opening 416, the opening 418, and the support structure 420, respectively. As shown in FIG. 4, the catheter body 412 may be connected directly to the distal tip 408 without the use of a recoil spring 316 (FIG. 3). In other implementations, the catheter 402 may include a recoil spring, similar to the recoil spring 316 of FIG. 3.

The hammer component 406 shown in FIG. 4 comprises a hollow bead-based hammer assembly. Specifically, the hammer component 406 may comprise multiple bead segments that are slidably threaded onto the trigger wire 410. The trigger wire 410 may pass through the hollow center of the individual bead segments. The individual bead segments, including the distal-most segment 422, may also be hollow to allow the wire guide 414 to pass through the hammer component 406. In some implementations, the hammer component 406 may be formed from multiple segments to allow the hammer component 406 to bend more easily in tortuous vasculatures. In other implementations, the hammer component 406 may be formed as a unitary component.

Figure 5:
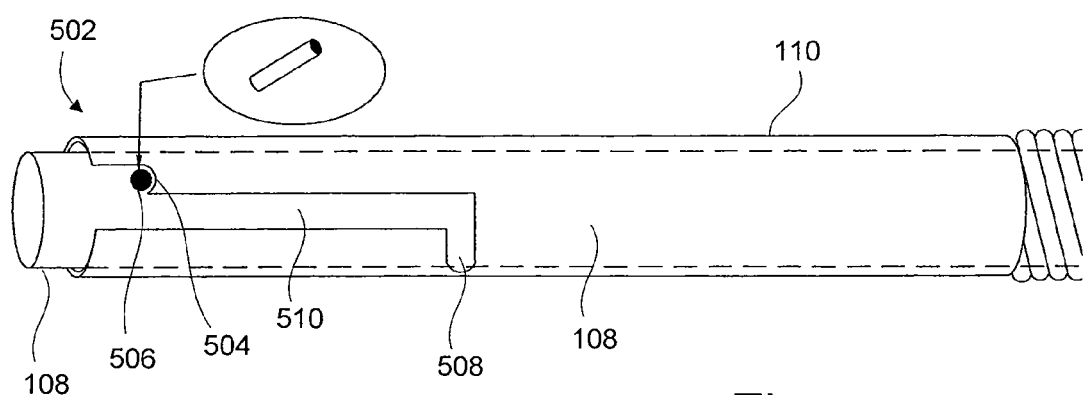
FIG. 5 illustrates a trigger mechanism for a spring action medical device.

FIG. 5 illustrates one embodiment of a trigger mechanism 502 for a spring action medical device. Although it may be used with any of the medical devices 102, 202, 302, and 402, the trigger mechanism 502 will be described with reference to the wire guide 102 of FIG. 1.

The trigger mechanism 502 is configured to hold the spring 104 (FIG. 1) in its compressed state and selectively release the spring 104 from the compressed state to push or propel the hammer component 106 forward in a distal direction. The trigger wire 108 is selectively engageable with the trigger mechanism 502. The trigger wire 108 may engage with the trigger mechanism 502 in a first position or a second position. When the trigger wire 108 is engaged with the trigger mechanism 502 in the first position, the spring 104 is placed in the compressed state. When the trigger wire 108 is engaged with the trigger mechanism 502 in the second position, the spring 104 is placed in a substantially relaxed state.

In one implementation, the trigger mechanism 502 includes a first recess 504 located on the outer wire guide body 110 at a predetermined location near the proximal end of the device. The first recess 504 is configured to receive and engage a protuberance 506 of the trigger wire 108 so as to hold the spring 104 in its compressed state. The location of the recess 504 may be selected to achieve the desired degree of compression when the spring 104 is in the compressed or loaded state. In implementations that desire a high degree of spring compression, the recess 504 may be located relatively close to the proximal end of the wire guide 102. In implementations that desire a lesser degree of spring compression, the recess 504 may be located relatively further from the proximal end of the wire guide 102.

The trigger mechanism 502 also includes a longitudinal slot 510 located on the outer wire guide body 110, the proximal end of the longitudinal slot 510 being adjacent to the first recess 504. The longitudinal slot 510 is configured to guide the protuberance 506 toward the first recess 504 when a user pulls the trigger wire 108 in a proximal direction to compress the spring from its substantially relaxed state. In operation, a user pulls the trigger wire 108 in a proximal direction to compress the spring until the protuberance 506 reaches the first recess 504, at which time the user twists the trigger wire 108 so as to position the protuberance 506 in the first recess 504. Subsequently, when the user releases the trigger wire 108, the protuberance 506 is engaged within first recess 504 under the bias of the spring so as to hold the spring in its compressed state. As shown in FIG. 5, the first recess 504 may include at least one concave inner surface to more reliably engage the protuberance 5 and prevent accidental dislodgment. When the user untwists the trigger wire 108 to remove the protuberance 506 from the first recess 504, the wire is released allowing the spring 104 to extend from the compressed state to propel the hammer component in a distal direction.

In some implementations, the trigger mechanism 502 may also include a second recess 508 located on the outer wire guide body 110 at a predetermined location adjacent to the distal end of the longitudinal slot 510 to hold the spring 104 in a substantially relaxed state when the protuberance 506 engages the second recess 508. In other implementations, the protuberance that engages with the first recess 504 may be different than the protuberance that engages with the second recess 508.

FIGS. 6a and 6b illustrate one embodiment of an actuator for a spring action medical device. Although it may be used with any of the medical devices 102, 202, 302, and 402, the actuator will be described with reference to the wire guide 102 of FIG. 1. The actuator includes a cap 602, a carriage piece 604, and one or more ramps 606. FIG. 6a shows a partial perspective view of the actuator. FIG. 6b is a representation of the path the carriage piece 604 of the actuator travels as it passes over a series of ramps. The multiple ramps illustrated in FIG. 6b may represent multiple different ramps of an actuator or may represent an actuator with a single ramp that the carriage piece 604 travels over multiple times.

To use the actuator with the wire guide 102 (FIG. 1), the trigger wire 108 of the wire guide 102 may be coupled with the carriage piece 604. A bottom surface 608 of the carriage piece 604 rides along the ramps 606 when the cap 602 is twisted. Twisting the cap 602 in the counterclockwise direction (FIG. 6a) causes the carriage piece 604 to rise when it rides up the ramp 606. Because the trigger wire 108 is coupled with the carriage piece 604, the trigger wire 108 is pulled in the proximal direction as the carriage piece 604 rides up the ramp 606. When the carriage piece 604 is riding up the ramp 606, the trigger wire 108 is pulling the hammer component 106 in the proximal direction which compresses the spring 104.

After the carriage piece 604 moves over the peak of the ramp 606, the carriage piece 604 will fall into a valley which releases the tension on the trigger wire 108. When the tension is released, the spring 104 is allowed to extend from the compressed state to propel the hammer component 106 forward in the distal direction. As the cap 602 continues to be twisted in the counterclockwise direction, the ramps 606 will cause the spring 104 to be sequentially compressed and released. Therefore, a user may cause multiple spring firings or strikes of the hammer by applying a twisting motion to the cap 602.

The actuator may also include a mechanism to turn the cap 602. The mechanism may be any component that can store an actuation force, such as a spring, rubber band, or the like. For example, a user may twist the cap 602 in a first direction to wind up the actuator. Upon release of the cap 602, the winding mechanism may cause the cap 602 to spin in the opposite direction until coming to rest. While the cap is spinning, the carriage piece 604 rises and falls as it rides up and over the ramps 606. As the carriage piece 604 rises and falls, the spring 104 will be sequentially compressed and released resulting in multiple spring firings or strikes of the hammer.

In other implementations, the actuator may comprise a motor which may be internally or externally powered. A user may employ the motor to spin the cap 602 over the ramps 606, pull the trigger wire 108, and/or directly compress/extend the spring 104.

FIG. 7 illustrates another embodiment of an actuator for a spring action medical device. The actuator includes an oscillation generator 702, a first pin vise 704, and a second pin vise 706. Although it may be used with any of the medical devices 102, 202, 302, and 402, the actuator will be described with reference to the wire guide 102.

The actuator may be coupled with a proximal end of the wire guide 102. The first pin vise 704 may connect with a first portion of the wire guide 102, such as the outer wire guide body 110. The second pin vise 706 may connect with a second portion of the wire guide 102, such as the trigger wire 108. The oscillation generator 702 may pull and then release the trigger wire 108 which compresses and releases the spring 104. Therefore, a user may cause multiple spring firings or strikes of the hammer through the oscillation generator 702. Alternatively, the oscillation generator 702 may actuate the hammer component 106 directly without use of a spring. The oscillation generator 702 may be a SouthOrd Lat-17 lock picking gun, or the like.

Figure 8:
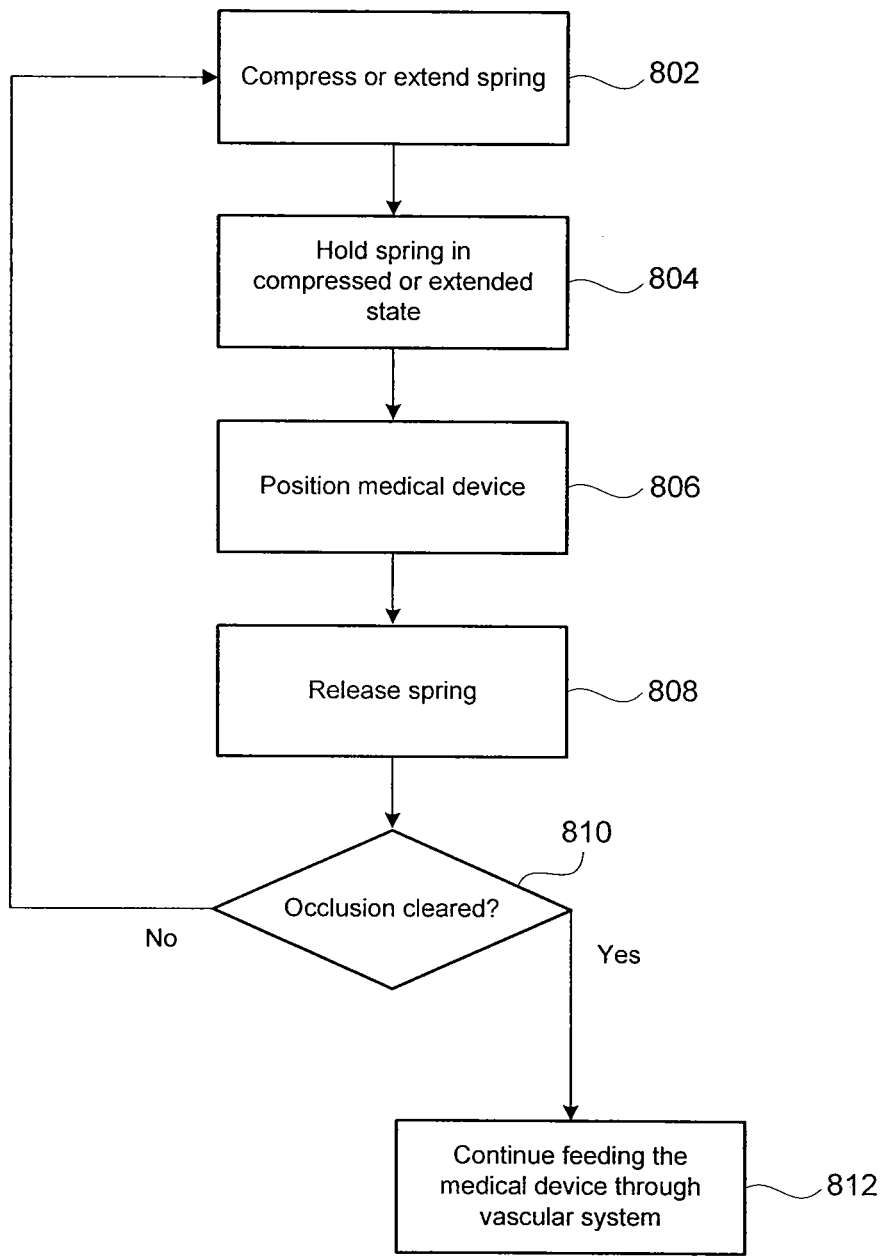
FIG. 8 shows a method of using a spring action medical device to pass through an occlusion.

FIG. 8 shows a method of using a spring action medical device to pass through an occlusion. An occlusion may be a partial or a total blockage in a vascular passage or other body lumen. The method of FIG. 8 will be described with reference to the wire guide 102 shown in FIG. 1. However, the method of FIG. 8 may also be performed with other spring action medical devices, such as the wire guide 202 shown in FIG. 2 or the catheters 302 and 402 shown in FIGS. 3 and 4.

At act 802, a spring of the medical device is compressed or stretched. The spring of the medical device may be compressed or stretched either before insertion of the device into the patient's vascular system or after insertion of the device into the patient's vascular system. In one implementation, a user may pull the trigger wire 108 of the wire guide 102 in a proximal direction to retract the hammer component 106 and place the spring 104 into a compressed state. The spring 104 may be compressed between the hammer component 106 and some other support structure, such as the support structure 120 formed on the inner surface of the outer wire guide body 110. In another implementation, the medical device may be configured with an extension spring. For example, a user may pull the trigger wire 108 in a proximal direction to place a relaxed spring into an extended state.

The amount of force that is provided by the spring is dependent on the amount of compression or extension in the spring. The user may control the amount of spring force created by controlling the amount of compression/extension provided to the spring. In one implementation, a small spring force may be desired. Therefore, the user may only compress/stretch the spring a relatively small amount. In other implementations, a larger spring force may be desired. Therefore, the user may compress/stretch the spring a relatively larger amount.

At act 804, the spring is held in the compressed or extended state. The user may engage the trigger wire 108 with a trigger mechanism to hold the spring in the compressed or extended state. In one implementation, the trigger mechanism includes a recess located on the outer wire guide body 110 at a predetermined location to hold the spring 104 in the compressed state when a protuberance of the trigger wire 108 engages the recess.

At act 806, the medical device is positioned within a body, such as in a patient's vascular system. The medical device may be positioned within a patient's vascular system at act 806 before and/or after the spring of the medical device is placed in the loaded state at act 802. For example, in one implementation, the user may first position the distal tip of the medical device to be near the occlusion before placing the spring in the loaded state. In another implementation, the spring may be placed in the loaded state before the distal tip is positioned to be near the occlusion.

The medical device may be positioned so that the distal tip 112 of the wire guide 102 is within a force transfer range of an occlusion in a body lumen, such as a vascular passage. The force transfer range may be the range of distances from which the distal tip may transfer a force to an occlusion in a body lumen in response to being actuated, such as being struck by a hammer component. In one implementation, a user may position the distal tip 112 of the wire guide 102 to be within a tip movement range of an occlusion in a vascular passage. The tip movement range may be the distance that the distal tip 112 travels in a distal direction when the hammer component 106 strikes the distal tip 112. In another implementation, the user may position the distal tip 112 to abut an occlusion in a vascular passage. Therefore, the distal tip 112 may transfer force to the occlusion even if the distal tip 112 is constrained from substantial movement in the distal direction, such as by the safety wire 114.

At act 808, the spring of the medical device is released from the compressed or extended state. If the triggering mechanism is used to hold the spring 104 in the extended state, the trigger wire may be released from the retracted position when the protuberance is disengaged from the recess which allows the spring 104 to push or propel the hammer component 106 forward in a distal direction. The spring may be configured to extend from the compressed state quickly. The quick movement of the spring may allow the distal tip to penetrate the occlusion. Because the distal tip may be positioned to be within the tip movement range (e.g., a force transfer range either through tip movement or direct force transfer without tip movement) of the occlusion at act 806, the distal tip may make contact with the occlusion, and/or transfer force to the occlusion, when the hammer component 106 strikes the distal tip. In some instances, the distal tip will make contact with the occlusion without passing through the occlusion. In other instances, the distal tip will pass through the occlusion.

At act 810, it is determined whether the occlusion has been sufficiently cleared. The user may determine whether a sufficiently large passage has been created by the spring action of the medical device. If the user determines that the occlusion has not been sufficiently cleared at act 810, then the spring may be recompressed/stretched at act 802 for a second attempt at clearing the occlusion. This recompression/stretching may occur while the distal tip remains within the patient. After one or more compressions/stretches and releases of the spring, the user may determine that the occlusion is sufficiently cleared. When that occurs, the user may continue feeding the medical device through the patient's vascular system to the desired destination at act 812. In some instances, the objective of the procedure may be to clear one or more occlusions. In that case, the medical device would be steered to the next occlusion and the spring action occlusion clearing process may begin again for the next occlusion.

Although the invention has been described and illustrated with reference to specific illustrative embodiments thereof, it is not intended that the invention be limited to those illustrative embodiments. For example, FIGS. 1-4 illustrate a distal end spring that is compressed and then released to perform the spring action. Other alternative embodiments could include a distal end spring that is stretched and then released, a proximal end spring that is stretched and then released, or a proximal end spring that is compressed and then released to perform the spring action. Also, various combinations of features are disclosed together in FIGS. 1-4. Those features may be combined together to form other embodiments. As one example, the bead-based hammer component 206 of FIG. 2 may be used together with a coil wire guide body 110 of FIG. 1. As another example, the sharpened distal tip 308 of FIG. 3 may replace the rounded distal tip 408 of FIG. 4. As yet another example, the recoil spring 316 of FIG. 3 may be used in the configurations illustrated in FIG. 1, 2, or 4 to allow the distal tip to travel in response to contact from the hammer component. Other combinations are also possible. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The medical devices described herein may be dimensioned to fit within a vascular passage or other body lumen. The wire guide may generally have a length in the range of 30-600 cm. In some implementations, the length of the wire guide may be in the range of 90-300 cm. The wire guide may generally have an outer diameter in the range of 0.204-1.321 mm (0.008-0.052 inches). In some implementations, the outer diameter may be in the range of 0.254-2.286 mm (0.01-0.09 inches). For example, one type of wire guide may have an outer diameter of about 0.889 mm (0.035 inches). A catheter may be dimensioned to receive a wire guide. The outer diameter of a catheter may be in the range of 2-36 French (Fr.). In some implementations, the outer diameter may be in the range of 4-8 Fr. For example, one type of catheter may have an outer diameter of 5 Fr.

What is claimed is:

1. A medical device, comprising:
   a body portion;
   a distal tip disposed at a distal end of the body portion;
   a spring;
   a support structure on an inner surface of the body portion; and
   a hammer component disposed between the distal tip and the spring, wherein the hammer component is movable relative to the distal tip between a first position and a second position, wherein the hammer component is spaced apart from the distal tip in the first position, and wherein the hammer component is in contact with the distal tip in the second position;
   a trigger wire coupled with the hammer component in a configuration where movement of the trigger wire in a proximal direction relative to the body portion retracts the hammer component and compresses the spring into a loaded state between the hammer component and the support structure;
   wherein the spring is configured to provide a force when released from a loaded state to propel the hammer component in a distal direction from the first position to the second position to strike the distal tip with the hammer component;
   wherein the distal tip is movable relative to the body portion in response to the hammer component striking the distal tip.

2. The medical device of claim 1, wherein the hammer component and the spring are disposed within the body portion;
   wherein a first end portion of the spring is coupled with the hammer component, a second end portion of the spring is coupled with a support structure of the body portion, and the spring is compressed between the hammer component and the support structure when the spring is in the loaded state.

3. The medical device of claim 1, wherein the hammer component comprises a distal-most segment and a second segment that is separate from the distal-most segment and movable relative to the distal-most segment; wherein the trigger wire passes through an opening in the second segment and is connected with the distal-most segment.

4. The medical device of claim 1, further comprising:
   an actuator base that comprises a ramped surface with at least one inclined ramp peak and at least one ramp valley; and
   an actuator carriage piece coupled with the trigger wire, wherein a surface of the actuator carriage piece is configured to travel along the ramped surface of the actuator base in response to a twisting motion applied to the actuator carriage piece.

5. The medical device of claim 4, wherein the actuator carriage piece is configured to pull the trigger wire in a proximal direction as the actuator carriage piece travels up the at least one inclined ramp peak of the actuator base; and
   wherein the actuator carriage piece is configured to release tension in the trigger wire as the actuator carriage piece falls from the at least one inclined ramp peak into the at least one ramp valley.

6. The medical wire guide of claim 1, further comprising a trigger mechanism configured to selectively engage the trigger wire to hold the spring in the loaded state, wherein the trigger mechanism is configured to selectively release the trigger wire to allow the spring to propel the hammer component in the distal direction.

7. The medical device of claim 1, further comprising an oscillation generator coupled with the trigger wire to pull and release the trigger wire.

8. The medical device of claim 1, further comprising a recoil spring;
   wherein the hammer component and the spring are disposed within the body portion;
   wherein a first end portion of the recoil spring is connected with the distal tip, a second end portion of the recoil spring is connected with a distal portion of the body portion, and the recoil spring is configured to stretch to allow a distal movement of the distal tip in response to contact between the hammer component and the distal tip.

9. The medical device of claim 1, further comprising a safety wire;
   wherein the hammer component and the spring are disposed within the body portion;
   wherein a first end portion of the safety wire is connected with the distal tip, a second end portion of the safety wire is connected with a proximal end portion of the body portion, and the safety wire is configured to limit a distal movement of the distal tip relative to the proximal end portion of the body portion.

10. The medical device of claim 1, wherein the body portion comprises a first opening that provides a path for a wire guide to pass into a proximal end of the body portion, pass through an opening in the spring, pass through an opening in the hammer component, and pass out of an opening in the distal tip.

11. The medical device of claim 10, wherein the body portion comprises a second opening configured to provide a path for a trigger wire to pass into a proximal end of the body portion, pass through the opening in the spring, and connect with the hammer component.

12. The medical device of claim 11, further comprising an expandable balloon coupled with the body portion, wherein the body portion comprises a third opening configured to provide access to an inner chamber of the balloon.

13. The medical device of claim 1, wherein the distal tip comprises a distal-most tip of a wire guide or a distal-most tip of a catheter; and
 wherein the distal tip is configured to transfer a force to an adjacent external object in response to contact between the hammer component and the distal tip.

14. The medical device of claim 1, further comprising a body portion, wherein the distal tip is attached to the body portion or is an integral portion of the body portion;
 wherein a proximal surface of the distal tip is located inside a cavity of the body portion and a distal surface of the distal tip is located outside the cavity of the body portion; and
 wherein the spring is configured to cause the hammer component to travel inside the cavity of the body portion relative to the distal tip when the spring is released from the loaded state, and cause the hammer component to strike the proximal surface of the distal tip within the cavity of the body portion.

15. A medical device, comprising:
 a body portion;
 a distal tip disposed at a distal end of the body portion;
 a support structure on an inner surface of the body portion;
 a hammer component that is movable relative to the distal tip between a first position and a second position, wherein the hammer component is spaced apart from the distal tip in the first position, and wherein the hammer component is in contact with the distal tip in the second position;
 a spring disposed between the hammer component and the support structure; and
 a trigger wire coupled with the hammer component in a configuration where movement of the trigger wire in a proximal direction relative to the body portion retracts the hammer component and compresses the spring into a loaded state between the hammer component and the support structure;
 wherein the spring is configured to provide a force when released from the loaded state to propel the hammer component in a distal direction relative to the body portion from the first position to the second position to strike the distal tip with the hammer component;
 wherein the distal tip is movable relative to the body portion in response to the hammer component striking the distal tip.

* * * * *